US010720038B1

(12) United States Patent
Wen (10) Patent No.: US 10,720,038 B1
(45) Date of Patent: Jul. 21, 2020

(54) EMERGENCY RESPONSE SYSTEMS AND METHODS OF USING THE SAME

(71) Applicant: Xiao Jun Wen, Norcross, GA (US)

(72) Inventor: Xiao Jun Wen, Norcross, GA (US)

(*) Notice: Subject to any disclaimer, the term of this patent is extended or adjusted under 35 U.S.C. 154(b) by 0 days.

(21) Appl. No.: 16/589,060

(22) Filed: Sep. 30, 2019

(51) Int. Cl.
| | |
|---|---|
| G08B 23/00 | (2006.01) |
| G08B 21/04 | (2006.01) |
| G08B 25/01 | (2006.01) |
| G10L 15/26 | (2006.01) |
| A61B 5/00 | (2006.01) |

(52) U.S. Cl.
CPC ........ *G08B 21/0453* (2013.01); *A61B 5/0022* (2013.01); *G08B 21/0476* (2013.01); *G08B 21/0492* (2013.01); *G08B 25/016* (2013.01); *G10L 15/265* (2013.01)

(58) Field of Classification Search
None
See application file for complete search history.

(56) References Cited

U.S. PATENT DOCUMENTS

| | | | | |
|---|---|---|---|---|
| 2012/0108917 A1* | 5/2012 | Libbus | ................. | A61B 5/0006 600/301 |
| 2013/0082837 A1* | 4/2013 | Cosentino | ............. | A61B 5/002 340/539.12 |

* cited by examiner

*Primary Examiner* — Adolf Dsouza
(74) *Attorney, Agent, or Firm* — Ming Jiang; MM IP Services LLC (57) ABSTRACT

The present disclosure relates to an emergency response system having an emergency response system server, a patient database, a communication system, and many patient response devices (PAD) for many patients. Each patient and each PAD are registered at emergency response system server and patient information is stored in patient database. When emergency occurs to a patient carrying PAD, patient presses an emergency button on PAD and PAD initiates an emergency call to emergency dispatch center to notify patient's GPS location and patient information. live emergency responder connects to one or more patient's helping hands and a medical facility to coordinate immediate medical assistance to the patient based on the patient information received and retrieved from the patient database. Patient specific medical assistance instructions are sent to patient, patient takes patient specific emergency medicines stored in PAD. The patient continues to communicate with the live emergency responder until ambulance arrives.

20 Claims, 6 Drawing Sheets

EMERGENCY RESPONSE SYSTEMS AND METHODS OF USING THE SAME

FIELD

The present disclosure generally relates to medical devices, and more particularly to emergency response systems and methods of using these emergency response systems.

BACKGROUND

According to World Health Organization (WHO), of the 56.9 million deaths worldwide in 2016, more than half (30.7 million or 54%) were due to these top three causes related to heart conditions, including ischemic heart diseases, stroke, and chronic obstructive pulmonary. Ischemic heart disease, stroke and chronic obstructive pulmonary are the world's biggest killers, accounting for a combined 18.2 million deaths in 2016. These diseases have remained the leading causes of death globally in the last 15 years.

Major of deaths from ischemic heart disease and stroke are preventable if patients call emergency medical care to get the patients to the emergency care in shortest time possible and take the appropriate medications immediately when patients start to notice some of symptoms of heart attacks and/or stroke. The most important things for a patient to survive include: the patient has access to and takes appropriate medications, the patient receives immediate professional care, and the patient is transferred to medical facilities as soon as possible before irreversible damages to the heart muscle and/or brain tissue occur.

Therefore, it is desirable to have an emergency response system to ensure: the patient receives immediate medical care by trained professionals, the patient receives and takes appropriate medications, and nearby emergency dispatch centers are notified, and ambulance and medical emergency staff arrive at the scene in shortest possible time.

Therefore, a heretofore unaddressed needs still exist in the art to address the aforementioned deficiencies and inadequacies.

SUMMARY

In one aspect, the present disclosure relates to an emergency response system. In certain embodiments, the emergency response system includes: an emergency response system server, a patient database, a communication system, and a group of patient response devices for a group of patients. Each patient and a corresponding patient response device each patient carries are registered at the emergency response system server and patient information of the registered patients is stored in the patient database. The emergency response system server provides immediate emergency assistance to each of the registered patient when emergencies occur.

In certain embodiments, the database is connected to and accessible by the emergency response system server. The patient database stores patient information of each registered patient. In certain embodiments, the patient information includes personal information, medical history, patient contact information, and contact information of one or more patient's helping hands to be notified of each registered patient. In certain embodiments, the patient's helping hands include, but not limited to, all family members, relatives, friends, neighbors, guardians, bystanders, local emergency or non-emergency medical facilities, community rescue members and trained CPR volunteers, and anyone who is nearby, and is able to help.

In certain embodiments, the communication system is connected to the emergency response system server. The communication system may provide voice, text, and video communication over a communication network among the patient, one or more live emergency responders from a nearby emergency dispatch center, one or more patient's helping hands on record, and one or more nearby medical facilities to provide immediate emergency assistance to the patient when emergency occurs.

In certain embodiments, each patient carries a corresponding patient response device. Each patient response device includes an emergency button for the patient to press and a voice-activated emergency call function to initiate at least voice communication with the emergency response system server and the communication system directly, and an emergency medicine storage for storing one or more patient specific emergency medicines to be used when emergency occurs.

In certain embodiments, an emergency response system indicator of a patient response device is lit in green light indicating the patient response device is in normal operation state. In one embodiment, when an emergency occurs to the patient who carries the patient response device, the patient presses the emergency button of the patient response device, the emergency response system indicator turns red indicating the patient is in an emergency. In another embodiment, when an emergency occurs to the patient who carries the patient response device, the patient speaks to the patient response device with a predetermined distinctive phrase to activate the emergency response device and the emergency response system indicator turns red indicating the patient is in an emergency. The patient response device initiates an emergency call to a nearby emergency dispatch center to notify a live emergency responder with the patient's GPS location information and patient information including contact information of one or more patient's helping hands on record. The live emergency responder connects to one or more patient's helping hands on record and a nearby medical facility to coordinate immediate medical assistance to the patient based on the patient information received and retrieved from the patient database. The live emergency responder and the emergency response system server provide patient specific medical assistance instructions for the patient to follow including instructing the patient to take one or more patient specific emergency medicines stored in the emergency medicine storage of the patient response devices either portable or stationary. The patient may continue to communicate with the live emergency responder and the one or more patient's helping hands on record until an ambulance from the nearby medical facility arrives. In case the patient is incapable to talk, the patient response devices will be beeping or having alarm soundings to alert or seek help from others surrounding the patient. In addition, the emergency response system sends text messages to update the patient's current status every few minutes to family members until the ambulance or the patient arrives to the emergency facility.

In certain embodiments, the communication network includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

In certain embodiments, the emergency response system server includes: a processor, a network interface controller, and a non-volatile memory. The processor manages operations of the entire emergency response system. The network interface controller connects to the communication network through a firewall connector over a firewall. The non-volatile memory stores an operating system, a network communication module, and an emergency response controller. The emergency response controller includes a patient information storage module for accessing the patient database through a database connector, a communication control module for facilitating communication to the communication system through a communication system connector, and computer executable instructions.

In certain embodiments, when executed by the processor, the computer executable instructions performs one or more of following operations: an emergency voice call is received from a patient response device through the communication system when the emergency button of the patient response device is pressed or voice-activated by a patient when an emergency occurs, the live emergency responder of a nearby emergency dispatch center is notified of emergency along with patient's GPS location information, and patient information including contact information of one or more patient's helping hands on record. The patient response device carried by the patient or stationed nearby the patient is connected to the patient's helping hands on record through the communication control module to coordinate immediate medical assistance to the patient, the patient information storage module retrieves patient information from the patient database, and the communication control module transmits a set of patient specific medical assistance instructions through the communication system connector and the live emergency responder for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives.

In certain embodiments, the patient response device includes at least a microphone and a speaker for the patient to make and receive voice calls. In certain embodiments, the patient response device further includes a display screen and a camera. In one embodiment, the patient uses the display screen to receive and display text messages. In another embodiment, the patient uses the camera and the display screen to carry out video calls.

In certain embodiments, the communication system connector includes: a voice input terminal connected to the voice input module, a text input terminal connected to the text input module, a video input terminal connected to the video input module, a voice output terminal connected to the voice output module, a text output terminal connected to the text output module, and a video output terminal connected to the video output module.

In certain embodiments, the communication among the patient, the live emergency responder, the patient's helping hands on record and the nearby medical facility includes: a mobile voice call, a mobile videotelephony call, a landline voice call, a videotelephony call over the Internet, a text message over a mobile phone, a text message over various social media platforms, and a videotelephony call over the social media platforms.

In certain embodiments, the communication system includes: a voice input module, a text input module, a video input module, a voice output module, a text output module, and a video output module.

The voice input module includes a mobile voice input interface to receive mobile voice calls, and a landline voice input interface to receive landline voice calls. It also can activate the emergency response device via voice activation whenever the patient is incapable to press the emergency call button. The text input module having a social media text input interface to receive text messages through the social media platforms, and a text message input interface to receive text messages through mobile phones. The video input module includes a mobile video input interface to receive video calls over the mobile phones, and a social media video input interface to receive video calls through the social media platforms.

The voice output module includes a mobile voice output interface to make mobile voice calls, and a landline voice output interface to make landline voice calls. The text output module includes a social media text output interface to transmit text messages through the social media platforms, and a text message output interface to transmit text messages through the mobile phones. The video output module includes a mobile video output interface to make video calls over the mobile phones, and a social media video output interface to make video calls through the social media platforms.

The communication system also includes: a speech to text conversion module for converting voice input to text input, a live emergency responder interface module for the live emergency responder to receive and make conference calls among the patient, the live emergency responder, the patient's helping hands on record and the nearby medical facility through voice calls, text messages, and video calls, and a text to speech conversion module to make voice calls to the patient through the patient response devices.

In certain embodiments, the patient response device includes: a processor, a network interface controller, the emergency medicine storage, and a non-volatile memory. The processor manages operations of the patient response devices. The network interface controller facilitates the communication among the patient response device, the emergency response system server and the communication system. The emergency medicine storage includes one or more emergency medicine compartments, where patient specific emergency medicines are stored. The non-volatile memory stores an operating system, a GPS module for detecting the GPS location of the patient carrying the patient response device, and a patient response device controller having a patient information storage module for storing the patient's information, a patient communication control module for facilitating communication through the network interface controller to the emergency response system server and the communication system over the communication network, and computer executable instructions.

In certain embodiments, when executed by the processor, the computer executable instructions performs one or more of following operations: the emergency button of the patient response device is pressed by the patient or the patient speaks to the patient response device with the predetermined distinctive phrase when an emergency occurs, the patient response device initiates an emergency call to a nearby emergency dispatch center to notify the live emergency responder with the patient's GPS location information and patient information including contact information of one or more patient's helping hands on record, the patient response device is connected to the patient's helping hands on record and a nearby medical facility through the patient communication control module to coordinate immediate medical assistance to the patient based on the patient information retrieved from the patient database and from the patient information storage module, the patient response device receives a set of patient specific medical assistance instructions from the live emergency responder for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives. The patient communication control module continues to send text messages every few minutes to notify all stakeholders as described above until the patient arrives to the emergency room or intentionally terminated by an emergency medical staff.

In one embodiment, the patient response device includes a portable patient response device to be carried with the patient. The portable patient response device stores one or more patient specific emergency medicines for the patient. In another embodiment, the patient response device includes a stationary patient response device to be placed at home or work place of the patient. The stationary patient response device stores one or more patient specific emergency medicines for the patient. In yet another embodiment, the patient response device includes multiple public stationary patient response devices. These public stationary patient response devices are placed in public places. Each of the public stationary patient response devices stores at least one of several common emergency medicines and a regular emergency response kit as well.

In another aspect, the present disclosure relates to a method of using an emergency response system. In certain embodiments, the method includes: registering, by a group of patients, a group of patient response devices at an emergency response system server of the emergency response system, one patient response device for each patient. The patient information of each of the patients is stored in a patient database of the emergency response system. The emergency response system includes a network of emergency dispatch centers to provide immediate emergency assistance to the patients when emergencies occur to them.

In certain embodiments, the method also includes: activating, by a patient, the patient response device carried by the patient when an emergency occurs to the patient, and an emergency response system indicator of the patient response device turns red indicating the patient is in an emergency. Activating the patient response device includes: pressing an emergency button on the patient response device, and speaking to the patient response device with a predetermined distinctive phrase. The method also includes, initiating, by the patient response device, an emergency call to a nearby emergency dispatch center to notify a live emergency responder with the patient's GPS location information and patient information including contact information of one or more patient's helping hands on record, and connecting, by the live emergency responder, to one or more patient's helping hands on record, and a nearby medical facility to coordinate immediate medical assistance to the patient based on the patient information received and retrieved from the patient database.

In certain embodiments, the method further includes: providing, by the live emergency responder and the emergency response system server, patient specific medical assistance instructions for the patient to follow including instructing the patient to take one or more patient specific emergency medicines stored in an emergency medicine storage of the patient response device, and communicating, by the patient through a communication system of the emergency response system, with the live emergency responder and the one or more patient's helping hands on record until an ambulance from the nearby medical facility arrives.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the present disclosure, and features and benefits thereof, and together with the written description, serve to explain the principles of the present invention. Wherever possible, the same reference numbers are used throughout the drawings to refer to the same or like elements of an embodiment, and wherein.

DETAILED DESCRIPTION

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the term "helping hands" is defined as, but not limited to: all family members, relatives, friends, neighbors, guardians, bystanders, local emergency or non-emergency medical facilities, community rescue members and trained CPR volunteers, and anyone who is nearby and able to help.

As used herein, the terms "comprising," "including," "carrying," "having," "containing," "involving," and the like are to be understood to be open-ended, i.e., to mean including but not limited to.

As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings FIGS. 1 through 6, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

Figure 1:
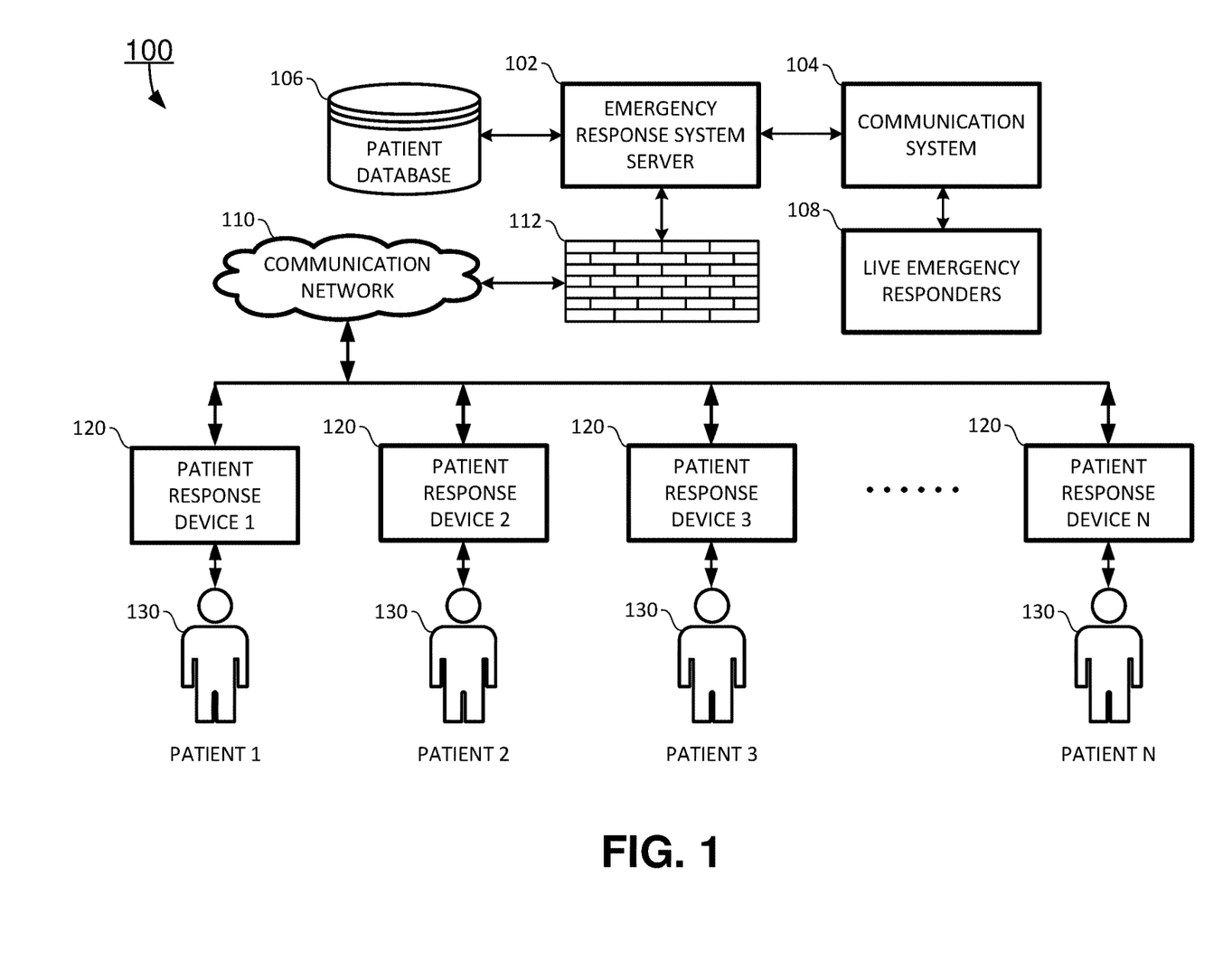
FIG. 1 shows a block diagram of an emergency response system according to certain embodiments of the present disclosure.

In one aspect, the present disclosure relates to an emergency response system 100 as shown in FIG. 1. In certain embodiments, the emergency response system 100 includes: an emergency response system server 102, a patient database 106, a communication system 104, and a group of patient response devices 120 for a group patient 130. Each patient 130 and each corresponding patient response device 120 the patient 130 carries are registered at the emergency response system server 102. Patient information of these registered patients 130 is stored in the patient database 106. The emergency response system server 102 provides immediate emergency assistance to each of the registered patient 130 when emergencies occur.

In certain embodiments, the patient database 106 is connected to and accessible by the emergency response system server 102. The patient database 106 stores patient information of each registered patient 130. In certain embodiments, the patient information includes personal information, medical history, patient contact information, and contact information of one or more patient's helping hands, and local medical facilities to be notified of each registered patient 130.

In certain embodiments, the communication system 104 is connected to the emergency response system server 102. The communication system 104 may provide voice, text, and video communication over a communication network 110 among the patient 130, one or more live emergency responders 1081 from a nearby emergency dispatch center 108, one or more patient's helping hands on record, and one or more nearby medical facilities to provide immediate emergency assistance to the patient when emergency occurs.

Figure 5:
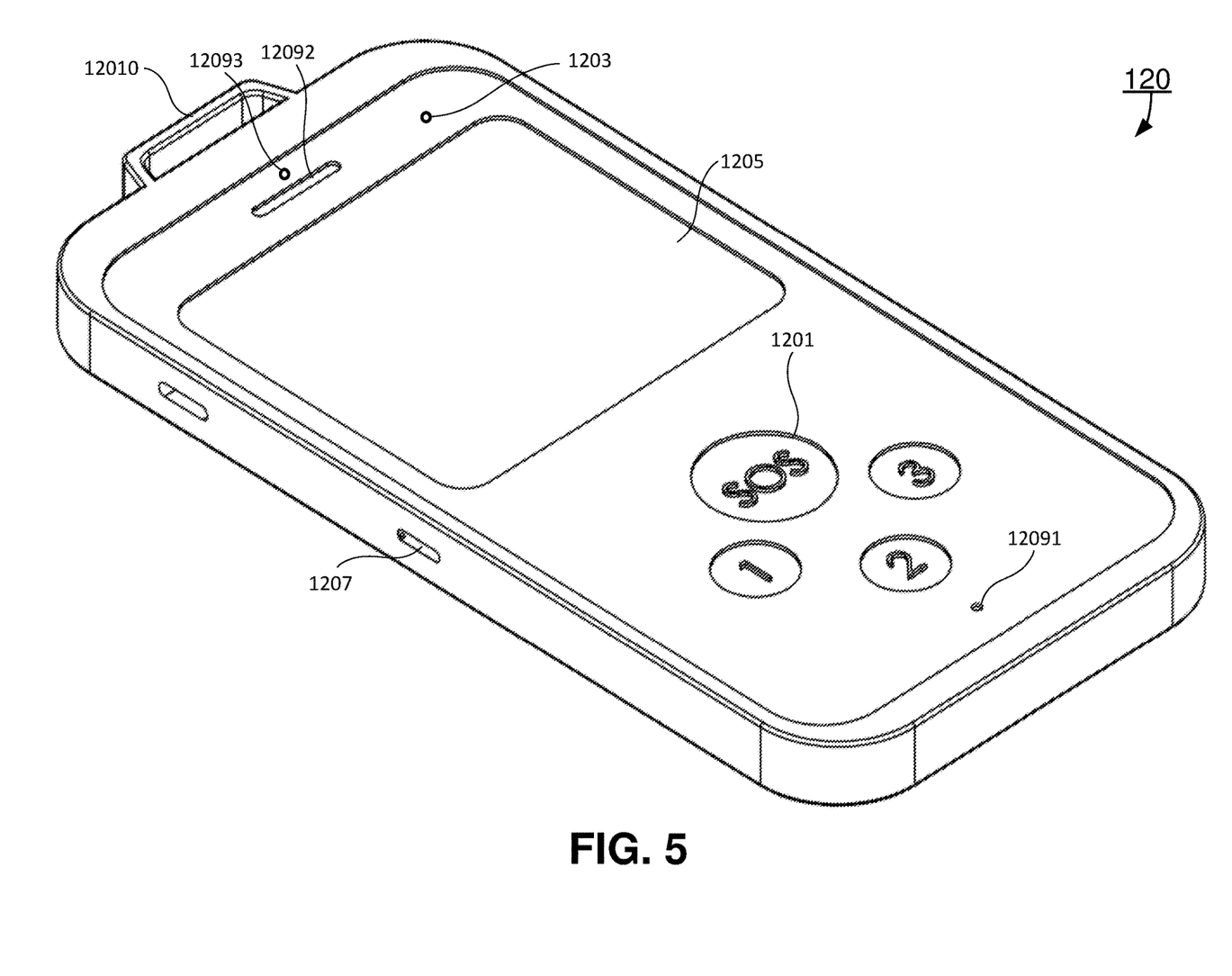
FIG. 5 shows an exemplary patient response device of the emergency response system according to certain embodiments of the present disclosure.

In certain embodiments, each patient 130 carries a corresponding patient response device 120 as shown in FIG. 5. Each patient response device 120 includes an emergency button 1201 for the patient 130 to press when emergency occurs. When the emergency button 1201 is pressed for a predetermined period of time by the patient 130, the patient response device 120 initiate at least voice communication with the emergency response system server 102 and the communication system 104 directly. In one embodiment, the predetermined period of time may be set as three seconds. When the patient 130 presses the emergency button 1201 for longer than three seconds, the patient response device 120 determines that the patient 130 does have an emergency. When the patient 130 presses the emergency button 1201 for less than three seconds, the patient response device 120 determines that the patient 130 does not have an emergency, and the emergency button 1201 was pressed by accident. This is designed to distinguish a real emergency and a false alarm.

In certain embodiments, each patient 130 carries the corresponding patient response device 120 as shown in FIG. 5. Each patient response device 120 includes a microphone 12091 for the patient 130 to activate the emergency response device 120 through a voice-activated emergency call function when an emergency occurs. To activate the emergency response device 120 through the voice-activated emergency call function, the patient 130 is required to speak to the microphone 12091 with a predetermined distinctive phrase to avoid false alarm by mis-activating the emergency response device 120 by noise around the patient 130. In one embodiment, the patient 130 may speak to the microphone: "hello, doctor", for example. Other phrase may be selected for different countries, or different languages. When the patient response device 120 receives the predetermined distinctive phrase, the patient response device 120 initiate at least voice communication with the emergency response system server 102 and the communication system 104 directly.

In certain embodiments, each patient response device 120 may also include an emergency medicine storage 1208 (not showing in FIG. 5) for storing one or more patient specific emergency medicines to be used when emergency occurs. In one embodiment, the patient specific emergency medicines include tissue plasminogen activator (tPA) for stroke/heart attack patients. In another embodiment, the patient specific emergency medicines include epinephrine for server allergic reaction patients. Various sizes of emergency medicine storage 1208 of patient response devices 120 may be available to accommodate various size emergency medicines for various high risk patients 130 with various known diseases.

In certain embodiments, as shown in FIG. 5, an emergency response system indicator 1203 of the patient response device 120 is lit in green light indicating the patient response device 120 is in normal operating state. In one embodiment, when an emergency occurs to the patient 130 who carries the patient response device 120, the patient 130 presses the emergency button 1201 of the patient response device 120 for longer than the predetermined period of time (for example three seconds), the emergency response system indicator 1203 turns red indicating the patient 130 is in an emergency. In one embodiment, when an emergency occurs to the patient 130 who carries the patient response device 120, the patient 130 presses the emergency button 1201 of the patient response device 120 for longer than the predetermined period of time (for example three seconds), the emergency response system indicator 1203 turns red indicating the patient 130 is in an emergency. In another embodiment, when an emergency occurs to the patient who carries the patient response device 120, the patient speaks to the microphone 12091 of the patient response device 120 with the predetermined distinctive phrase to activate the emergency response device 120 and the emergency response system indicator 1203 turns red indicating the patient 130 is in an emergency.

In certain embodiments, as shown in FIG. 5, the patient response device 120 includes a SIM card slot 1207 for connecting a SIM card for mobile communication networks.

Then the patient response device 120 initiates an emergency call to the nearby emergency dispatch center 108 to notify a live emergency responder 1081 with the patient's GPS location information and patient information including contact information of one or more patient's helping hands on record. The live emergency responder 1081 connects to one or more patient's helping hands on record, and a nearby medical facility to coordinate immediate medical assistance to the patient 130 based on the patient information received and retrieved from the patient database 106. The live emergency responder 1081 and the emergency response system server 102 may provide patient specific medical assistance instructions for the patient 130 to follow. These patient specific medical assistance instructions may include instruction to the patient to take one or more patient specific emergency medicines stored in the emergency medicine storage 1208 of the patient response device 120. The patient 130 continues to communicate with the live emergency responder 1081 and the one or more patient's helping hands on record until an ambulance from the nearby medical facility arrives. In case the patient 130 is incapable to talk, the patient response device 120 will be beeping or having alarm soundings to alert or seek help from others surrounding the patient 130. In addition, the emergency response system 100 may send text messages to update the patient's current status every few minutes to all helping hands until the ambulance or the patient arrives to the emergency facility.

In certain embodiments, the communication network 110 includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

Figure 2:
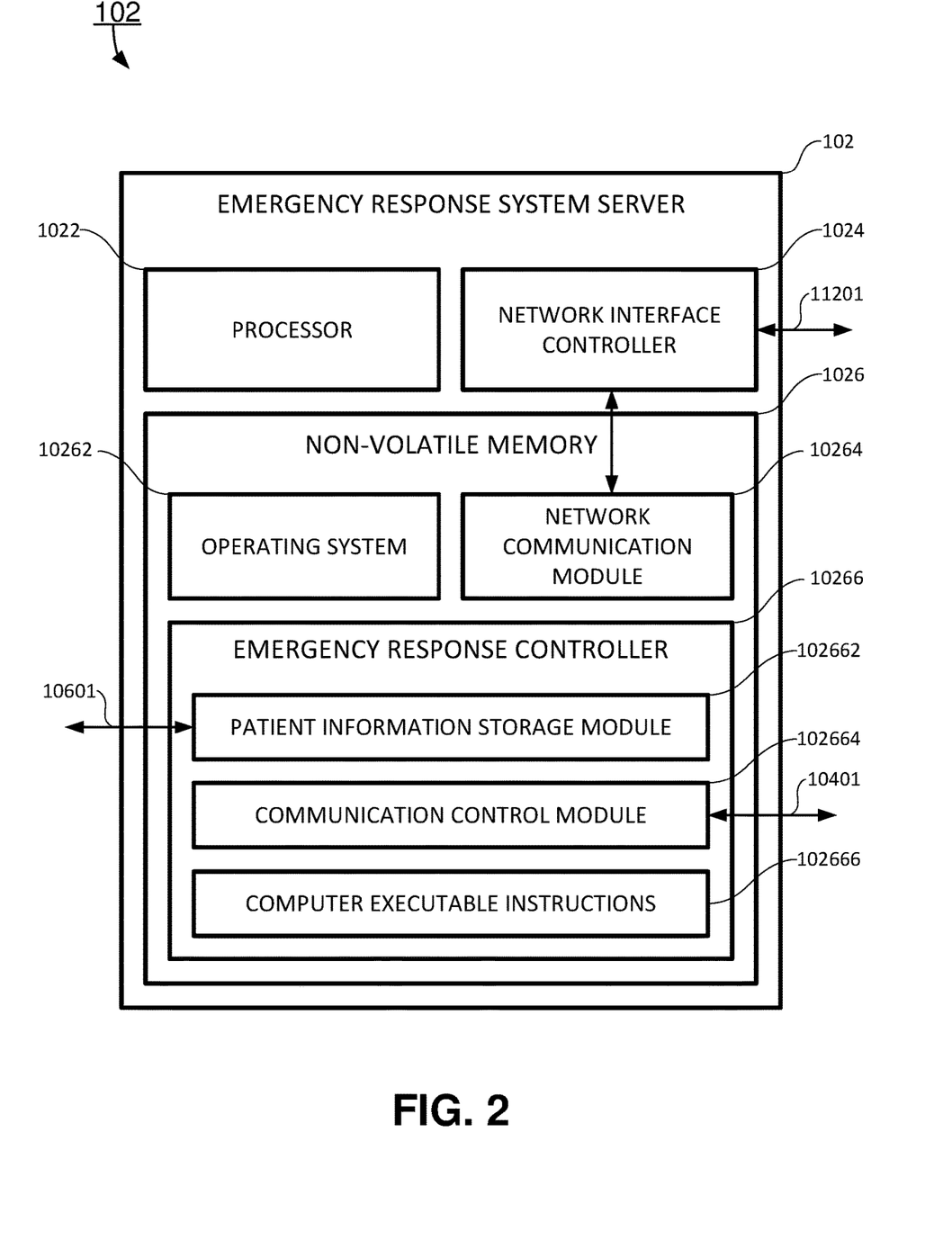
FIG. 2 illustrates a block diagram of an emergency response system server of the emergency response system according to certain embodiments of the present disclosure.

In certain embodiments, as shown in FIG. 2, the emergency response system server 102 includes: a processor 1022, a network interface controller 1024, and a non-volatile memory 1026. The processor 1022 manages operations of the entire emergency response system 100. The network interface controller 1024 connects to the communication network 110 through a firewall connector 11201 over a firewall 112. The non-volatile memory 1026 stores an operating system 10262, a network communication module 10264, and an emergency response controller 10266. The emergency response controller 10266 includes a patient information storage module 102662 for accessing the patient database 106 through a database connector 10601, a communication control module 102664 for facilitating communication to the communication system 104 through a communication system connector 10401, and computer executable instructions 102666.

In certain embodiments, when executed by the processor 1022, the computer executable instructions 102666 performs one or more of following operations, not necessarily in the following order:

an emergency voice call is received from the patient response device 120 through the communication system 104 when the patient response system 120 is activated by patient 130;

the live emergency responder 1081 of the nearby emergency dispatch center 108 is notified of emergency along with patient's GPS location information, and patient information including contact information of one or more patient's helping hands on record;

the patient response device 120 carried by the patient 130 is connected to the patient's helping hands on record and a nearby medical facility through the communication control module 102664 to coordinate immediate medical assistance to the patient 130;

the patient information storage module 102662 retrieves patient information from the patient database 106;

the communication control module 102664 transmits a set of patient specific medical assistance instructions through the communication system connector 10401 and the live emergency responder 1081 for the patient 130 to follow including instructing the patient to take one or more patient specific emergency medicines stored in the emergency medicine storage 1208 of the patient response device 120; and the patient 130 continues to communicate with the live emergency responder 1081 and the one or more patient's helping hands on record until an ambulance from the nearby medical facility arrives.

In one embodiment, the patient response device 120 is activated by the patient 130 pressing the emergency button 1201 of the patient response device 120. In another embodiment, the patient response device 120 is activated by the patient 130 speaking to the microphone 12091 of the patient response device 120 with the predetermined distinctive phrase.

Figure 3:
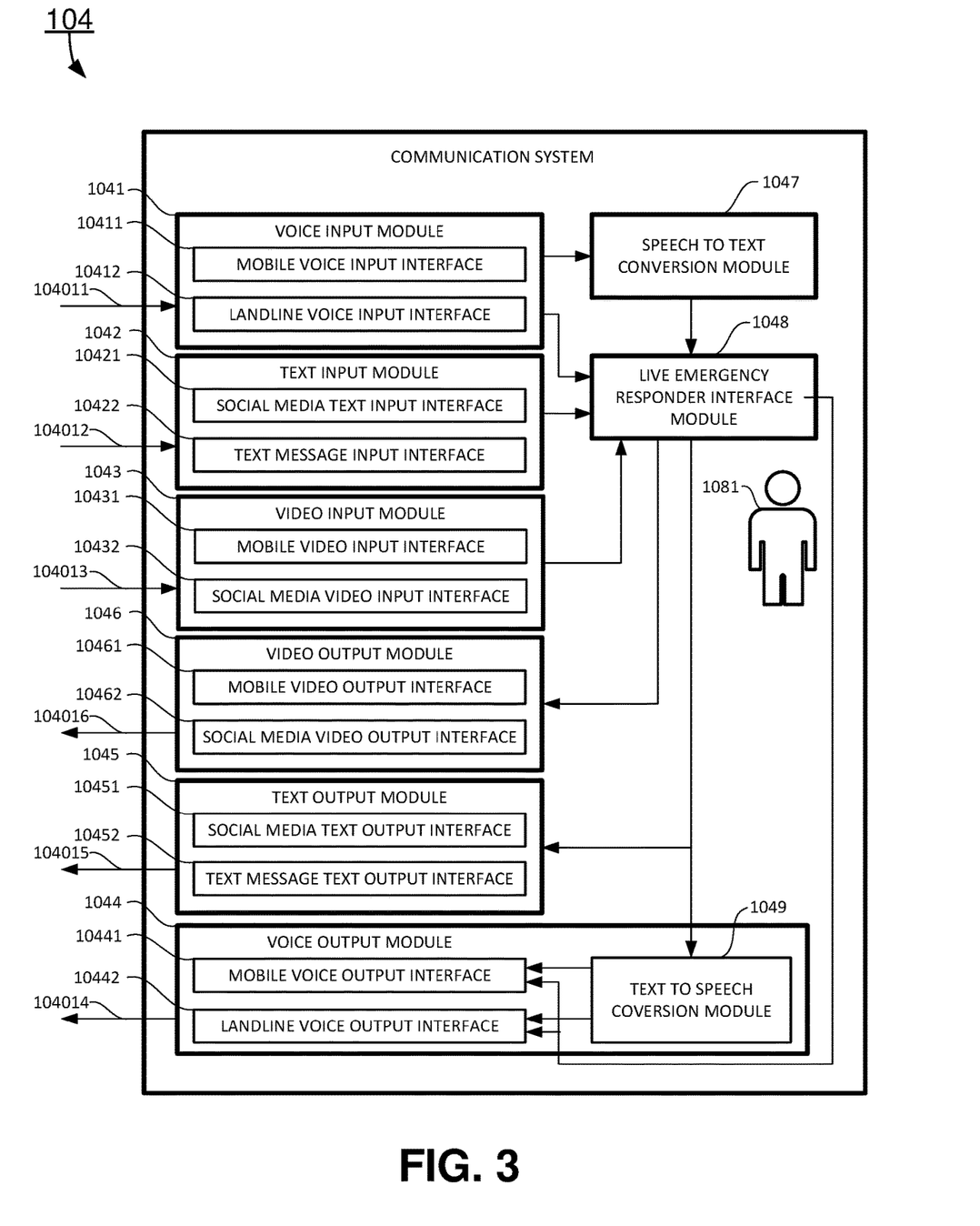
FIG. 3 illustrates a block diagram of a communication system of the emergency response system according to certain embodiments of the present disclosure.

In certain embodiments, as shown in FIG. 3, the communication system 104 includes: a voice input module 1041, a text input module 1042, a video input module 1043, a voice output module 1044, a text output module 1045, and a video output module 1046.

In certain embodiments, the voice input module 1041 includes a mobile voice input interface 10411 to receive mobile voice calls, and a landline voice input interface 10412 to receive landline voice calls. The text input module 1042 having a social media text input interface 10421 to receive text messages through the social media platforms, and a text message input interface 10422 to receive text messages through mobile phones. The video input module 1043 includes a mobile video input interface 10431 to receive video calls over the mobile phones, and a social media video input interface 10432 to receive video calls through the social media platforms.

In certain embodiments, the voice output module 1044 includes a mobile voice output interface 10441 to make mobile voice calls, and a landline voice output interface 10442 to make landline voice calls. The text output module 1045 includes a social media text output interface 10451 to transmit text messages through the social media platforms, and a text message output interface 10452 to transmit text messages through the mobile phones. The video output module 1046 includes a mobile video output interface 10461 to make video calls over the mobile phones, and a social media video output interface 10462 to make video calls through the social media platforms.

In certain embodiments, the communication system 104 also includes: a speech to text conversion module 1047 for converting voice input to text input, a live emergency responder interface module 1048 for the live emergency responder 1081 to receive and make conference calls among the patient 130, the live emergency responder 1081, the patient's helping hands on record and the nearby medical facility through voice calls, text messages, and video calls, and a text to speech conversion module 1049 to make voice calls to the patient 130 through the patient response device 120.

In certain embodiments, the communication system connector 10401 includes: a voice input terminal 10411 connected to the voice input module 1041, a text input terminal 104012 connected to the text input module 1042, a video input terminal 104013 connected to the video input module 1043, a voice output terminal 104014 connected to the voice output module 1044, a text output terminal 104015 connected to the text output module 1045, and a video output terminal 104016 connected to the video output module 1046.

In certain embodiments, the communication among the patient 130, the live emergency responder 1081, the patient's helping hands on record and the nearby medical facility includes: a mobile voice call, a mobile videotelephony call, a landline voice call, a videotelephony call over the Internet, a text message over a mobile phone, a text message over various social media platforms, and a videotelephony call over the social media platforms.

Figure 4:
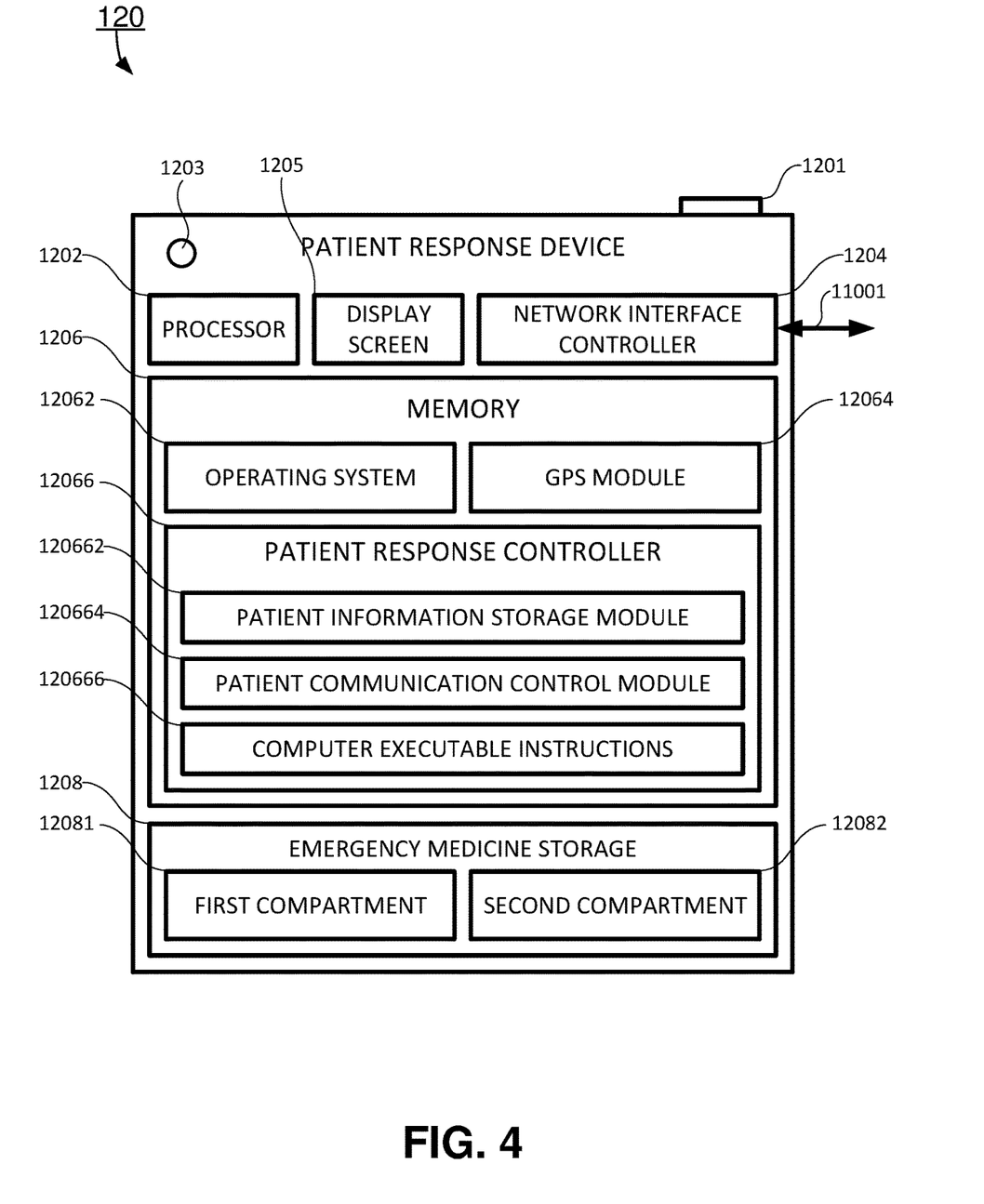
FIG. 4 illustrates a block diagram of a patient response device of the emergency response system according to certain embodiments of the present disclosure.

In certain embodiments, as shown in FIG. 4, the patient response device 120 includes: a processor 1202, a network interface controller 1204, the emergency medicine storage 1208, and a non-volatile memory 1206. The processor 1202 manages operations of the patient response device 120. The network interface controller 1204 facilitates the communication among the patient response device 120, the emergency response system server 102 and the communication system 104. The emergency medicine storage 1208 includes one or more emergency medicine compartments. In one embodiment, the emergency medicine storage 1208 includes a first compartment 12081 and a second compartment 12082. These emergency medicine compartments are used to store the patient specific emergency medicines. Various sizes of emergency medicine storage 1208 of patient response devices 120 may be available to accommodate various size emergency medicines for various high-risk patients 130 with various known diseases.

In certain embodiments, the non-volatile memory 1206 stores an operating system 12062, a GPS module 12064 for detecting the GPS location of the patient 130 carrying the patient response device 120, and a patient response device controller 12066 having a patient information storage module 120662 for storing the patient's information, a patient communication control module 120664 for facilitating communication through the network interface controller 1204 to the emergency response system server 102 and the communication system 104 over the communication network 110, and computer executable instructions 120666.

In certain embodiments, when executed by the processor 1202, the computer executable instructions 120666 performs one or more of following operations, not necessarily in the following order:

the patient response device 120 is activated by the patient 130 by pressing the emergency button 1201 of the patient response device 120, or speaking to the microphone 12091 of the patient response device 120 with the predetermined distinctive phrase, when an emergency occurs;

the patient response device 120 initiates an emergency call to the nearby emergency dispatch center 108 to notify the live emergency responder 1081 with the patient's GPS location information and patient information including contact information of one or more patient's helping hands on record;

the patient response device 120 is connected to the patient's helping hands on record and a nearby medical facility through the patient communication control module 120664 to coordinate immediate medical assistance to the patient 130 based on the patient information retrieved from the patient database 106 and from the patient information storage module 120662;

the patient response device 120 receives a set of patient specific medical assistance instructions from the live emergency responder 1081 for the patient 130 to follow including instructing the patient to take one or more patient specific emergency medicines stored in the emergency medicine storage 1208 of the patient response device 120; and the patient 130 continues to communicate with the live emergency responder 1081 and the one or more patient's helping hands on record until an ambulance from the nearby medical facility arrives.

In certain embodiments, as shown in FIG. 5, the patient response device 120 includes at least a microphone 12091 and a speaker 12092 for the patient 130 to make and receive voice calls. In certain embodiments, the patient response device 120 further includes a display screen 1205, and a camera 12093. In one embodiment, the patient 130 uses the display screen 1205 to receive and display text messages. In another embodiment, the patient 130 uses the camera 12093 and the display screen 1205 to carry out video calls. In certain embodiments, as shown in FIG. 5, the patient response device 120 includes a SIM card holder 1207 to hold a SIM card for mobile communication capable patient response device 120. The patient response device 120 may further include a lanyard holder 12010 for attaching the patient response device 120 to the patient 130 using a lanyard.

In certain embodiments, the social media platforms include, but not limited to: Facebook, Youtube, WhatsApp, Messenger, WeChat, Instagram, QQ, Tumblr, Qzone, Tik Tok, Sina Weibo, Twitter, Reddit, Baidu Tieba, LinkedIn, Viber, Snappchat, and Pinterest and various combination of these social media platforms.

In one embodiment, the patient response device 120 includes a portable patient response device to be carried with the patient 130. The portable patient response device stores one or more patient specific emergency medicines for the patient 130. In another embodiment, the patient response device 120 includes a stationary patient response device to be placed at home or work place of the patient 130. The stationary patient response device stores one or more patient specific emergency medicines for the patient 130. In yet another embodiment, the patient response device 120 includes multiple public stationary patient response devices. These public stationary patient response devices are placed in public places. Each of the public stationary patient response devices stores at least one of several common emergency medicines.

Figure 6:
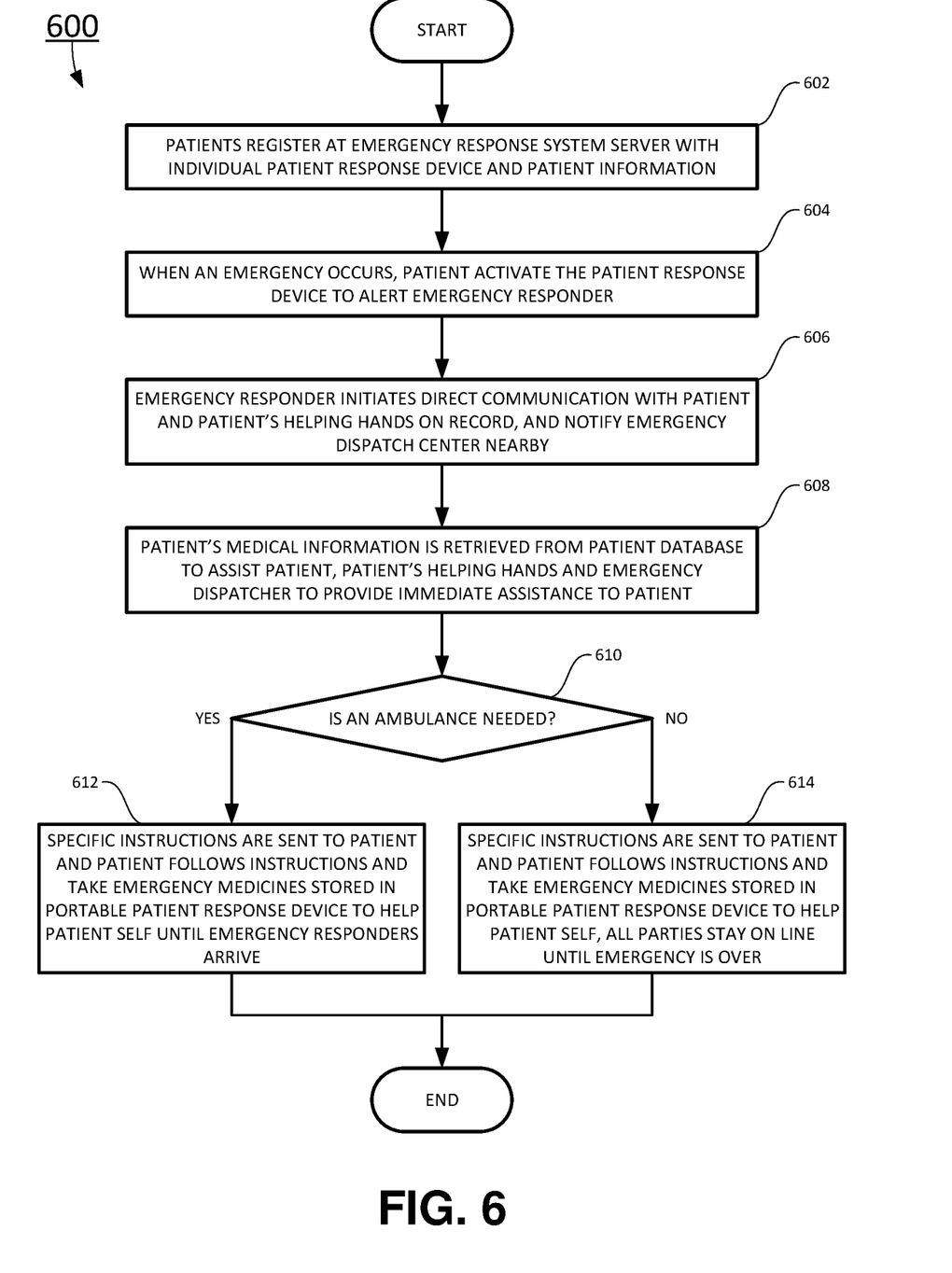
FIG. 6 shows a flow chart of a method of using the emergency response system according to certain embodiments of the present disclosure.

In another aspect, the present disclosure relates to a method 600 of using an emergency response system 100 as shown in FIG. 6.

In certain embodiments, as shown in FIG. 1, the emergency response system 100 includes: the emergency response system server 102, the patient database 106, the communication system 104, and multiple patient response devices 120. The emergency response system server 102 provides immediate emergency assistance to the patients 130 when emergencies occur. The patient database 106 is connected and accessible by the emergency response system server 102. The patient database 106 stored patient information of the patients 130. In certain embodiments, the patient information includes personal information, medical history, patient contact information, and contact information of one or more patient's helping hands on record and local medical facilities to be notified of each of the patients 130. The communication system 104 is connected to the emergency response system server 102. The communication system 104 may provide voice, text, and video communication over a communication network 110 among the patient, one or more live emergency responders 1081 from the nearby emergency dispatch center 108, one or more patient's helping hands on record, and one or more nearby medical facilities to provide immediate emergency assistance to the patient when emergency occurs. Each of the patients 130 carries one corresponding patient response device 120. In one embodiment, each of the patient response devices 120 includes: the emergency button 1201 for the patient 130 to press to initiate at least voice communication with the emergency response system server 102 and the communication system 104 directly. In another embodiment, each of the patient response devices 120 includes: the microphone 12091 for the patient 130 to speak to the patient response device 120 with the predetermined distinctive phrase to initiate at least voice communication with the emergency response system server 102 and the communication system 104 directly.

In certain embodiments, each of the patient response devices 120 includes: the emergency medicine storage 1208 for storing one or more patient specific emergency medicines to be used when emergency occurs.

In certain embodiments, the communication network 110 includes a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

In certain embodiments, as shown in FIG. 2, the emergency response system server 102 includes: a processor 1022, a network interface controller 1024, and a non-volatile memory 1026. The processor 1022 manages operations of the emergency response system 100. The network interface controller 1024 connects to the communication network 110 through a firewall connector 11201 over a firewall 112. The non-volatile memory 1026 stores an operating system 10262, a network communication module 10264, and an emergency response controller 10266. The emergency response controller 10266 includes a patient information storage module 102662 for accessing the patient database 106 through a database connector 10601, a communication control module 102664 for facilitating communication to the communication system 104 through a communication system connector 10401, and computer executable instructions 102666.

In certain embodiments, as shown in FIG. 3, the communication system 104 includes: a voice input module 1041 having a mobile voice input interface 10411 to receive mobile voice calls, and a landline voice input interface 10412 to receive landline voice calls, a text input module 1042 having a social media text input interface 10421 to receive text messages through various social media platforms, and a text message input interface 10422 to receive text messages through mobile phones, a video input module 1043 having a mobile video input interface 10431 to receive video calls over the mobile phones, and a social media video input interface 10432 to receive video calls through the social media platforms, a voice output module 1044 having a mobile voice output interface 10441 to make mobile voice calls, and a landline voice output interface 10442 to make landline voice calls, a text output module 1045 having a social media text output interface 10451 to transmit text messages through the social media platforms, and a text message output interface 10452 to transmit text messages through the mobile phones, a video output module 1046 having a mobile video output interface 10461 to make video calls over the mobile phones, and a social media video output interface 10462 to make video calls through the social media platforms.

In certain embodiments, the communication system 104 further includes: a speech to text conversion module 1047 for converting voice input to text input; a live emergency responder interface module 1048 for the live emergency responder 1081 to receive and make conference calls among the patient 130, the live emergency responder 1081, the patient's helping hands on record, and the nearby medical facility through voice calls, text messages, and video calls, and a text to speech conversion module to make voice calls to the patient 130 through the patient response device 120.

In certain embodiments, as shown in FIGS. 4 and 5, the patient response device 120 includes at least a microphone 12091 and a speaker 12092 for the patient 130 to make and receive voice calls. In certain embodiments, the patient response device 120 further includes a display screen 1205 and a camera 12093. In one embodiment, the patient 130 uses the display screen 1205 to receive and display text messages. In another embodiment, the patient 130 uses the camera 12093 and the display screen 1205 to carry out video calls.

In certain embodiments, the communication among the patient 130, the live emergency responder 1081, the patient's helping hands on record, and the nearby medical facility includes: a mobile voice call, a mobile videotelephony call, a landline voice call, a videotelephony call over the Internet, a text message over a mobile phone, a text message over the social media platforms, and a videotelephony call over the social media platforms.

In one embodiment, the patient response device 120 includes a portable patient response device to be carried with the patient 130. The portable patient response device stores one or more patient specific emergency medicines for the patient 130. In another embodiment, the patient response device 120 includes a stationary patient response device to be placed at home or work place of the patient 130. The stationary patient response device 120 stores one or more patient specific emergency medicines for the patient 130. In yet another embodiment, the patient response device 120 includes multiple public stationary patient response devices 120. These public stationary patient response devices 120 are placed in public places. Each of the public stationary patient response devices 120 stores at least one of several common emergency medicines.

FIG. 6 shows a flow chart of the method 100 of using the emergency response system 120 according to certain embodiments of the present disclosure.

At block 602, each of a group of patients 130 register the patient 130 self, a corresponding patient response device 120 at the emergency response system server 102 of the emergency response system 100, one patient response device 120 for each patient 130, and individual patient information. The patient information of each of the patients 130 is stored in a patient database 106 of the emergency response system 100. The emergency response system 100 includes a network of emergency dispatch centers 108 to provide immediate emergency assistance to the patients 130 when emergencies occur to the registered patients 130.

At block 604, when an emergency occurs to the patient 130, the patient 130 activates the patient response device 120. In one embodiment, the patient 130 activates the patient response device 120 by pressing the emergency button 1201 of the patient response device 120 carried by the patient 130 to alert one or more live emergency responders 1081. In another embodiment, the patient 130 activates the patient response device 120 by speaking to the microphone 12091 of the patient response device 120 carried by the patient 130 with the predetermined distinctive phrase to alert one or more live emergency responders 1081. An emergency response system indicator 1203 of the patient response device 120 turns red indicating the patient 130 is in an emergency.

At block 606, the patient response device 120 initiates an emergency call to a nearby emergency dispatch center 108 to notify the live emergency responder 1081 with the patient's GPS location information and patient information including contact information of one or more patient's helping hands on record.

At block 608, the patient 130's medical information is received by the emergency response system server 102 from the patient response device 120 and retrieved from the patient database to assist the patient 130, the patient's helping hands on record, and the live emergency responder 1081 to provide immediate assistance to the patient 130.

At query block 610, the live emergency responder 1081 determines whether an ambulance is needed. If the ambulance is needed is needed, the method 600 proceeds to block 612. Otherwise, the method 600 proceeds to block 614.

At block 612, when the ambulance is needed, the live emergency responder 1081 notifies the nearby emergency medical facility to send the ambulance and patient specific professional staffs to assist the patient 130. In the meantime, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the patient response device 120, until the ambulance and the patient specific professional staffs arrive.

At block 614, when the ambulance is not needed, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the patient response device 120. The patient 130 stays online with the live emergency responder 1081, the patient's helping hands on record, and emergency medical staff until the emergency is over.

The foregoing description of the exemplary embodiments of the disclosure has been presented only for the purposes of illustration and description and is not intended to be exhaustive or to limit the disclosure to the precise forms disclosed. Many modifications and variations are possible considering the above teaching.

The embodiments were chosen and described in order to explain the principles of the disclosure and their practical application to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. An emergency response system, comprising:
   an emergency response system server, wherein each of a plurality of patients and a corresponding patient response device each patient carries are registered at the emergency response system server, and the emergency response system server provides immediate emergency assistance to each of the plurality of patients when emergencies occur;

a patient database connected to and accessible by the emergency response system server, wherein the patient database stores patient information of the plurality of patients, wherein the patient information comprises personal information, medical history, patient contact information, and contact information of one or more patient's helping hands and local medical facilities to be notified of each patient;

a communication system connected to the emergency response system server, wherein the communication system provides voice, text, and video communication over a communication network among the patient, one or more live emergency responders from a nearby emergency dispatch center, one or more patient's helping hands on record, and one or more nearby medical facilities to provide immediate emergency assistance to the patient when emergency occurs; wherein the patient's helping hands include all family members, relatives, friends, neighbors, guardians, bystanders, local emergency or non-emergency medical facilities, community rescue members and trained CPR volunteers, and anyone who is nearby and is able to offer assistance, and a plurality of patient response devices, wherein each patient carries a corresponding patient response device, and each patient response device comprises an emergency button and a microphone for the patient to activate the patient response device and initiate at least voice communication with the emergency response system server and the communication system directly, and an emergency medicine storage for storing one or more patient specific emergency medicines to be used when emergency occurs, wherein an emergency response system indicator of a patient response device is lit in green light indicating the patient response device is in normal operation state, when an emergency occurs to a patient, the patient activate the patient response device, the emergency response system indicator turns red indicating the patient is in an emergency, the patient response device initiates an emergency call to the nearby emergency dispatch center to notify a live emergency responder with the patient's GPS location information and patient information including contact information of one or more patient's helping hands on record, the live emergency responder connects to one or more patient's helping hands on record and a nearby medical facility to coordinate immediate medical assistance to the patient based on the patient information received and retrieved from the patient database, and the live emergency responder and the emergency response system server provide patient specific medical assistance instructions for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives.

2. The emergency response system according to claim 1, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

3. The emergency response system according to claim 2, wherein the emergency response system server comprises:
a processor, wherein the processor manages operations of the emergency response system;
a network interface controller connected to the communication network through a firewall connector over a firewall; and
a non-volatile memory, wherein the non-volatile memory stores an operating system, a network communication module, and an emergency response controller having a patient information storage module for accessing the patient database through a database connector, a communication control module for facilitating communication to the communication system through a communication system connector, and computer executable instructions, when executed by the processor, the computer executable instructions performs one or more of following operations:
at least an emergency voice call is received from a patient response device through the communication system when the patient response device is activated by the patient when an emergency occurs;
the live emergency responder of the nearby emergency dispatch center is notified of emergency along with patient's GPS location information, and patient information including contact information of one or more patient's helping hands on record;
the patient response device carried by the patient is connected to the patient's helping hands on record and a nearby medical facility through the communication control module to coordinate immediate medical assistance to the patient;
the patient information storage module retrieves patient information from the patient database;
the communication control module transmits a set of patient specific medical assistance instructions through the communication system connector and the live emergency responder for the patient to follow including instructing the patient to take one or more patient specific emergency medicines stored in the emergency medicine storage of the patient response device, and the patient continues to communicate with the live emergency responder and the one or more patient's helping hands on record until an ambulance from the nearby medical facility arrives.

4. The emergency response system according to claim 3, wherein the patient response device comprises at least a microphone and a speaker for the patient to make and receive voice calls.

5. The emergency response system according to claim 4, wherein the patient response device further comprises a display screen to receive and display text messages and a camera to carry out video calls.

6. The emergency response system according to claim 1, wherein the communication among the patient, the live emergency responder, the patient's helping hands on record and the nearby medical facility comprises:
a mobile voice call;
a mobile videotelephony call;
a landline voice call;
a videotelephony call over the Internet;
a text message over a mobile phone;

a text message over a plurality of social media platforms; and a videotelephony call over the plurality of social media platforms.

7. The emergency response system according to claim 6, wherein the communication system comprises:
- a voice input module having a mobile voice input interface to receive mobile voice calls, and a landline voice input interface to receive landline voice calls;
- a text input module having a social media text input interface to receive text messages through the plurality of social media platforms, and a text message input interface to receive text messages through mobile phones;
- a video input module having a mobile video input interface to receive video calls over the mobile phones, and a social media video input interface to receive video calls through the plurality of social media platforms;
- a voice output module having a mobile voice output interface to make mobile voice calls, and a landline voice output interface to make landline voice calls;
- a text output module having a social media text output interface to transmit text messages through the plurality of social media platforms, and a text message output interface to transmit text messages through the mobile phones;
- a video output module having a mobile video output interface to make video calls over the mobile phones, and a social media video output interface to make video calls through the plurality of social media platforms;
- a speech to text conversion module, wherein the speech to text conversion module converts voice input to text input;
- a live emergency responder interface module, wherein the live emergency responder uses the live emergency responder interface module to receive and make conference calls among the patient, the live emergency responder, the patient's helping hands on record and the nearby medical facility through voice calls, text messages, and video calls; and
- a text to speech conversion module, wherein the text to speech conversion module is used by the user to make voice calls to the patient through the patient response device.

8. The emergency response system according to claim 7, wherein the communication system connector comprises:
- a voice input terminal connected to the voice input module;
- a text input terminal connected to the text input module;
- a video input terminal connected to the video input module;
- a voice output terminal connected to the voice output module;
- a text output terminal connected to the text output module; and
- a video output terminal connected to the video output module.

9. The emergency response system according to claim 7, wherein the patient response device comprises:
- a processor, wherein the processor manages operations of the patient response device;
- a network interface controller, wherein the network interface controller facilitates the communication among the patient response device, the emergency response system server and the communication system;
- the emergency medicine storage, wherein the emergency medicine storage comprises one or more emergency medicine compartments, where one or more patient specific emergency medicines for the patient are stored; and
- a non-volatile memory, wherein the non-volatile memory stores an operating system, a GPS module for detecting the GPS location of the patient carrying the patient response device, and a patient response device controller having a patient information storage module for storing the patient's information, a patient communication control module for facilitating communication through the network interface controller to the emergency response system server and the communication system over the communication network, and computer executable instructions, when executed by the processor, the computer executable instructions performs one or more of following operations:
- the patient response device is activated by the patient, wherein the patient response device is activated by the patient by pressing the emergency button of the patient response device, and by speaking to the microphone of the patient response device with the predetermined distinctive phrase when an emergency occurs;
- the patient response device initiates an emergency call to the nearby emergency dispatch center to notify the live emergency responder with the patient's GPS location information and patient information including contact information of one or more patient's helping hands on record;
- the patient response device is connected to the patient's helping hands on record and a nearby medical facility through the patient communication control module to coordinate immediate medical assistance to the patient based on the patient information retrieved from the patient database and from the patient information storage module;
- the patient response device receives a set of patient specific medical assistance instructions from the live emergency responder for the patient to follow including instructing the patient to take one or more patient specific emergency medicines stored in the emergency medicine storage of the patient response device; and
- the patient continues to communicate with the live emergency responder and the one or more patient's helping hands on record until an ambulance from the nearby medical facility arrives.

10. The emergency response system according to claim 9, wherein the patient response device comprises:
- a portable patient response device to be carried with the patient wherein the portable patient response device stores one or more patient specific emergency medicines;
- a stationary patient response device to be placed at home or work place of the patient wherein the stationary patient response device stores one or more patient specific emergency medicines; and
- a plurality of public stationary patient response devices to be placed in public places wherein each of the plurality of public stationary patient response devices stores at least one of a plurality of common emergency medicines.

11. A method of using an emergency response system, comprising:
- registering, by a plurality of patients, each of the plurality of patients, and a plurality of patient response devices, one corresponding patient response device for each patient, at an emergency response system server of the emergency response system, wherein patient information of each of the plurality of patients is stored in a patient database of the emergency response system, and the emergency response system comprises a network of emergency dispatch centers to provide immediate emergency assistance to the plurality of patients when emergencies occur to them;

activating, by a patient, the patient response device carried by the patient when an emergency occurs to the patient, and an emergency response system indicator of the patient response device turns red indicating the patient is in an emergency, wherein activating the patient response device comprises: pressing an emergency button on the patient response device, and speaking to a microphone of the patient response device with a predetermined distinctive phrase;

initiating, by the activated patient response device, an emergency call to a nearby emergency dispatch center to notify a live emergency responder with the patient's GPS location information and patient information including contact information of one or more patient's helping hands on record, wherein the patient's helping hands include all family members, relatives, friends, neighbors, guardians, bystanders, local emergency or non-emergency medical facilities, community rescue members and trained CPR volunteers, and anyone who is nearby and is able to offer assistance;

connecting, by the live emergency responder, to one or more patient's helping hands on record and a nearby medical facility to coordinate immediate medical assistance to the patient based on the patient information received and retrieved from the patient database;

providing, by the live emergency responder and the emergency response system server, patient specific medical assistance instructions for the patient to follow including instructing the patient to take one or more patient specific emergency medicines stored in an emergency medicine storage of the patient response device; and communicating, by the patient through a communication system of the emergency response system, with the live emergency responder and the one or more patient's helping hands on record until an ambulance from the nearby medical facility arrives.

12. The method of claim 11, wherein the emergency response system comprises:

the emergency response system server, wherein each of the plurality of patients and a corresponding patient response device each patient carries are registered at the emergency response system server, and the emergency response system server provides immediate emergency assistance to each of the plurality of patients when emergencies occur;

the patient database connected to and accessible by the emergency response system server, wherein the patient database stores patient information of the plurality of patients, wherein the patient information comprises personal information, medical history, patient contact information, and contact information of one or more patient's helping hands on record and local medical facilities to be notified of each of the plurality of patients;

the communication system connected to the emergency response system server, wherein the communication system provides voice, text, and video communication over a communication network among the patient, one or more live emergency responders from the nearby emergency dispatch center, one or more patient's helping hands on record, and one or more nearby medical facilities to provide immediate emergency assistance to the patient when emergency occurs; and the plurality of patient response devices, wherein each of the plurality of patients carries one corresponding patient response device, and each of the plurality of patient response devices comprises the emergency button for a patient to press to initiate at least voice communication with the emergency response system server and the communication system directly, and the microphone for the patient to speak to the patient response device to initiate at least voice communication with the emergency response system server and the communication system directly, and the emergency medicine storage for storing one or more patient specific emergency medicines to be used when emergency occurs.

13. The method of claim 12, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

14. The method of claim 13, the emergency response system server comprises:

a processor, wherein the processor manages operations of the emergency response system;

a network interface controller connected to the communication network through a firewall connector over a firewall; and a non-volatile memory, wherein the non-volatile memory stores an operating system, a network communication module, and an emergency response controller having a patient information storage module for accessing the patient database through a database connector, a communication control module for facilitating communication to the communication system through a communication system connector, and computer executable instructions, when executed by the processor, the computer executable instructions performs one or more of following operations:

an emergency voice call is received from a patient response device through the communication system when the patient response device is activated by the patient when an emergency occurs, wherein the patient response device is activated by the patient by pressing the emergency button of the patient response device, and by speaking to the microphone of the patient response device with the predetermined distinctive phrase;

the live emergency responder of the nearby emergency dispatch center is notified of emergency along with patient's GPS location information and patient information including contact information of one or more patient's helping hands on record;

the patient response device carried by the patient is connected to the patient's helping hands on record and a nearby medical facility through the communication control module to coordinate immediate medical assistance to the patient;

the patient information storage module retrieves patient information from the patient database;

the communication control module transmits a set of patient specific medical assistance instructions through the communication system connector and the live emergency responder for the patient to follow, while the patient takes the patient specific emergency medicines stored in the emergency medicine storage of the patient response device; and the patient continues to communicate with the live emergency responder and one or more patient's helping hands on record until an ambulance from the nearby medical facility arrives.

15. The method of claim 14, wherein the patient response device comprises at least a microphone and a speaker for the patient to make and receive voice calls.

16. The method of claim 15, wherein the patient response device further comprises a display screen to receive and display text messages and a camera to carry out video calls.

17. The method of claim 16, wherein the communication system comprises:
- a voice input module having a mobile voice input interface to receive mobile voice calls, and a landline voice input interface to receive landline voice calls;
- a text input module having a social media text input interface to receive text messages through the plurality of social media platforms, and a text message input interface to receive text messages through mobile phones;
- a video input module having a mobile video input interface to receive video calls over the mobile phones, and a social media video input interface to receive video calls through the plurality of social media platforms;
- a voice output module having a mobile voice output interface to make mobile voice calls, and a landline voice output interface to make landline voice calls;
- a text output module having a social media text output interface to transmit text messages through the plurality of social media platforms, and a text message output interface to transmit text messages through the mobile phones;
- a video output module having a mobile video output interface to make video calls over the mobile phones, and a social media video output interface to make video calls through the plurality of social media platforms;
- a speech to text conversion module, wherein the speech to text conversion module converts voice input to text input;
- a live emergency responder interface module, wherein the live emergency responder uses the live emergency responder interface module to receive and make conference calls among the patient, the live emergency responder, the patient's helping hands on record and the nearby medical facility through voice calls, text messages, and video calls; and
- a text to speech conversion module, wherein the text to speech conversion module is used by the user to make voice calls to the patient through the patient response device.

18. The method of claim 17, wherein the communication among the patient, the live emergency responder, the patient's helping hands on record and the nearby medical facility comprises:
- a mobile voice call;
- a mobile videotelephony call;
- a landline voice call;
- a videotelephony call over the Internet;
- a text message over a mobile phone;
- a text message over a plurality of social media platforms; and
- a videotelephony call over the plurality of social media platforms; and wherein the communication system connector comprises:
- a voice input terminal connected to the voice input module;
- a text input terminal connected to the text input module;
- a video input terminal connected to the video input module;
- a voice output terminal connected to the voice output module;
- a text output terminal connected to the text output module; and
- a video output terminal connected to the video output module.

19. The method of claim 18, wherein the patient response device comprises:
- a processor, wherein the processor manages operations of the patient response device;
- a network interface controller, wherein the network interface controller facilitates the communication among the patient response device, the emergency response system server and the communication system;
- the emergency medicine storage, wherein the emergency medicine storage comprises one or more emergency medicine compartments, where one or more patient specific emergency medicines for the patient are stored; and
- a non-volatile memory, wherein the non-volatile memory stores an operating system, a GPS module for detecting the GPS location of the patient carrying the patient response device, and a patient response device controller 12066 having a patient information storage module for storing the patient's information, a patient communication control module for facilitating communication through the network interface controller to the emergency response system server and the communication system over the communication network, and computer executable instructions, when executed by the processor, the computer executable instructions performs one or more of following operations:
  - the patient response device is activated by the patient when an emergency occurs, wherein the patient response device is activated by the patient by pressing the emergency button of the patient response device, and by speaking to the microphone of the patient response device with the predetermined distinctive phrase;
  - the patient response device initiates an emergency call to the nearby emergency dispatch center to notify the live emergency responder with the patient's GPS location information and patient information including contact information of one or more patient's helping hands on record;
  - the patient response device is connected to the patient's helping hands on record and a nearby medical facility through the patient communication control module to coordinate immediate medical assistance to the patient based on the patient information from the patient information storage module;
  - the patient response device receives a set of patient specific medical assistance instructions from the live emergency responder for the patient to follow; and
  - the patient takes the patient specific emergency medicines stored in the emergency medicine storage; and waits for an ambulance dispatched from the nearby emergency dispatch center to arrive.

20. The method of claim 19, wherein the patient response device comprises:

a portable patient response device to be carried with the patient wherein the portable patient response device stores one or more patient specific emergency medicines;

a stationary patient response device to be placed at home or work place of the patient wherein the stationary patient response device stores one or more patient specific emergency medicines; and a plurality of public stationary patient response devices to be placed in public places wherein each of the plurality of public stationary patient response devices stores at least one of a plurality of common emergency medicines.

* * * * *